United States Patent [19]

Dawson

[11] Patent Number: 5,310,543
[45] Date of Patent: May 10, 1994

[54] LIQUID DENTIFRICES

[75] Inventor: Peter L. Dawson, Upton, United Kingdom

[73] Assignee: Chesebrough-Pond's USA Co., Division of Conopco, Inc., Greenwich, Conn.

[21] Appl. No.: 977,303

[22] Filed: Nov. 16, 1992

[30] Foreign Application Priority Data

Nov. 19, 1991 [GB] United Kingdom ............... 9124538

[51] Int. Cl.$^5$ ............................................. A61K 7/16
[52] U.S. Cl. ........................................................ 424/49
[58] Field of Search ................................ 424/49–58

[56] References Cited

U.S. PATENT DOCUMENTS

| | | | |
|---|---|---|---|
| 3,506,757 | 4/1970 | Salzmann | 427/52 |
| 3,705,940 | 12/1972 | Kirchgassner . | |
| 3,935,307 | 1/1976 | Aimoto et al. | 424/56 |
| 4,108,978 | 8/1978 | Mazzanobile et al. | 424/49 |
| 4,469,673 | 9/1984 | Iioka et al. | 424/50 |
| 4,528,181 | 7/1985 | Morton et al. . | |
| 4,565,692 | 1/1986 | Mulvey et al. . | |
| 4,618,488 | 10/1986 | Maeyama et al. . | |
| 4,772,461 | 9/1988 | Parran, Jr. et al. | 424/52 |
| 4,877,602 | 10/1989 | Uematsu et al. | 424/49 |
| 4,885,155 | 12/1989 | Parran, Jr. et al. | 424/52 |
| 5,032,387 | 7/1991 | Hill et al. | 424/49 |
| 5,149,521 | 9/1992 | Hirose et al. | 424/58 |
| 5,178,869 | 1/1993 | Ebine et al. | 424/401 |
| 5,188,821 | 2/1993 | Gaffar et al. | 424/52 |

FOREIGN PATENT DOCUMENTS

| | | |
|---|---|---|
| 1039656 | 10/1978 | Canada . |
| 0517319 | 12/1992 | European Pat. Off. . |
| 3527280 | 2/1986 | Fed. Rep. of Germany . |
| 675632 | 5/1966 | France . |
| 1600227 | 7/1970 | France . |
| 2232304 | 1/1975 | France . |
| 2556962 | 6/1985 | France . |
| 2240473 | 8/1991 | United Kingdom . |
| 2240473A | 8/1991 | United Kingdom . |

*Primary Examiner*—Shep K. Rose
*Attorney, Agent, or Firm*—Milton L. Honig

[57] ABSTRACT

The invention relates to liquid dentifrices which contain particulate siliceous abrasive cleaning agents, stably suspended in a liquid medium with the aid of a polysaccharide gum as suspending agent. By using a particulate siliceous abrasive cleaning agent with a specific surface area of between 50 and 900 m$^2$/g, and using a liquid medium which is free from polyol-type humectants, liquid dentifrices are obtained with satisfactory rheological properties. Preferably the compositions have a compositional viscosity index of between 3 and 30, said index being defined as $$\frac{20-S}{P},$$

wherein S=concentration in % of thickening silica, if present, in the liquid medium and P=concentration in % of polysaccharide gum in the liquid medium.

6 Claims, No Drawings

LIQUID DENTIFRICES

The present invention relates to liquid dentifrices which contain a particulate siliceous abrasive cleaning agent, stably suspended in a liquid medium.

More particularly it relates to liquid dentifrices which contain a particulate siliceous abrasive cleaning agent having a specific surface area, as measured by the BET method based on nitrogen adsorption, of between 50 and 900 m$^2$/g, stably suspended in a liquid medium that is substantially free from polyol-type humectants, with the aid of a polysaccharide gum as suspending agent.

Liquid dentifrices comprising particulate abrasive materials, stably suspended in an aqueous liquid vehicle with the aid of a polysaccharide gum as suspending agent have already been described in U.S. Pat. No. 3,506,737 (Salzmann). The particulate abrasive materials, mentioned in this reference, include finely powdered silica, but this abrasive material is not further specified or exemplified in this reference. Most of the exemplified formulations in this reference contain either a polyol-type humectant, or ethanol, both of which are not desired in the liquid dentifrices of the present invention, because they interfere with the required rheological properties of the liquid dentifrices. In addition, these ingredients increase the costs of liquid dentifrices.

In the published UK Patent Application GB 2,240,473 (Lion) liquid dentifrices are described which comprise silica or another particulate abrasive material having a specific surface area of up to 100 m$^2$/g, uniformly dispersed in an aqueous medium, optionally in the presence of a binder such as a mixture of a xanthan gum and a polyacrylate. These liquid dentifrices should have a viscosity of 2-18 Pa.s and a yield value of 1-60 Pa at 25° C. under specified conditions.

The preferred specific surface area of the abrasive material according to this reference ranges from 5-30 m$^2$/g, and the liquid dentifrices preferably contain a polyol-type humectant to achieve the required viscosity and yield value. In the examples, various abrasives are exemplified, and where silica is used, it is a precipitated silica with a specific surface area of 40 m$^2$/g in formulations that also contain a polyol-type humectant. A comparative example with such silica, or with a silica with a specific surface area of 200 m$^2$/g did not however have the required rheological properties.

Consequently, there still exists a need for a cost-effective, efficacious liquid dentifrice which remains stable over longer storage periods and possesses the required rheological properties.

It has now been found that such cost-effective, efficacious liquid dentifrice can be obtained, if a siliceous particulate abrasive material with a specific surface area of between 50 and 900 m$^2$/g is suspended in a aqueous liquid medium which is substantially free from polyol-type humectants, with the aid of a polysaccharide gum as suspending agent. Such liquid dentifrices remain stable over longer storage periods and possess the required rheological properties.

The invention will hereunder be described in more detail.

The siliceous particulate abrasive cleaning agent of the present invention embraces abrasive precipitated silicas, silica xerogels, silica aerogels and pyrogenic silicas, and they should have a dental abrasive value (determined by the B.S. DAV method 5136:81 using 10% w/w aqueous slurries) of between 20 and 80.

These abrasive silicas should have an average particle size (as measured using the Malvern Mastersizer) of between 1-15 μm, preferably between 3-12 μm. The abrasive silicas should have a specific surface area, as measured by the BET method based on nitrogen adsorption, of between 50-900 m$^2$/g, preferably 70-750 m$^2$/g and particularly preferably 80-700 m$^2$/g. They should have a pore volume, as measured by nitrogen and mercury porosimetry, of between 0.2 and 0.6 l/kg. Typical examples of particulate abrasive silicas suitable in the present invention are silica xerogels such as Gasil 200 TP ex Crosfields (specific surface area 699 m$^2$/g; pore volume 0.23 l/kg; average particle size 8-12 μm; DAV 55), precipitated silicas such as Zeodent 113 ex Huber Corp., (specific surface area 121 m$^2$/g; average particle size 8-10 μm; DAV 30; pore volume 0.4 l/kg) Tixosil 73 ex Rhone-Poulenc (specific surface area 60 m$^2$/g; average particle size 8 μm).

We have found that when using abrasive silicas, it is often advantageous to use these in conjunction with a thickening silica, which usually has a specific surface area in the range of abt. 100-400 m$^2$/g. Such thickening silicas differ from abrasive silicas in that they have a much higher pore volume in the range of 1.0-2.2 l/kg, as measured by nitrogen and mercury porosimetry.

Typical examples of thickening silicas which may be used together with the abrasive silicas are precipitated silicas such as Sident 22 S ex Rhone-Poulenc (specific surface area 174 m$^2$/g; pore volume > 1.23 l/kg; average particle size 7 μm); Tixosil 343 ex Rhone-Poulenc (specific surface area 215 m$^2$/g; average particle size 6-7 μm; pore volume > 1.34 l/kg) and so on.

The amount of the abrasive silica used in the present invention may range from 2-50% by weight, preferably from 5-45% by weight and particularly preferably from 5-25% by weight.

When thickening silicas are also used, their amount may usefully range from 5-15% by weight of the composition.

The liquid medium in which the particulate abrasive silicas are stably suspended should be substantially aqueous and should be substantially free from polyol-type humectants, i.e. should contain less than 5% by weight of a polyol-humectant such as sorbitol, glycerol, polyethylene glycol and the like. Furthermore the aqueous medium should contain less than 10% by weight dissolved solids.

The suspending agent which is used to stably suspend the particulate abrasive silicas in the aqueous liquid medium is of the polysaccharide gum type. Such polysaccharide gums are well-known, and they embrace xanthan gums, guar gums, karaya and tragacanth gums, carragheenan, cellulose derivatives such as sodium carboxymethylcellulose, etc. Mixtures of several polysaccharide gums may also be used. Preferred are the xanthan gums, either alone or in admixture with guar gums, and sodium carboxymethylcellulose, the former being preferred over the latter.

The amount of the polysaccharide gum may usually vary from 0.25-2% by weight, preferably from 0.3-1.5% by weight. In order to achieve the required rheological properties of the liquid dentifrices, the relative amounts of the thickening silica, if present, and the polysaccharide gum should be chosen such that the compositional viscosity index (cvi)

$$\frac{20 - S}{P}$$

should have a value of between 3-30, preferably between 3-15, whereby

S = concentration in % of thickening silica in the aqueous medium, and

P = concentration in % of polysaccharide gum in the aqueous medium.

Within these cvi ranges, the liquid dentifrices have been found to have a sufficient "hold" on the brush, while simultaneously having sufficient low stress viscosity to maintain stability, yet strongly shear thinning to aid manufacture and dispensing.

Thus, the compositions of the invention should have a viscosity of at least 50 Pa.s (at 25° C. and 0.1 sec$^{-1}$) to "hold" on standard toothbrush bristles for at least 5 minutes, and should have a viscosity of no more than 500 Pa.s (at 25° C. and 0.1 sec$^{-1}$) to enable easy manufacture, filling and dispensing from suitable containers.

The stable compositions of the invention exhibit low stress Newtonian viscosity plateaus of about 1500 Pa.s (measured by controlled stress viscoelastic rheometry).

They typically have a viscosity of between 50 and 500 Pa.s at 25° C. at a shear rate of 0.1 sec.$^{-1}$, preferably between 100-400 Pa.s. Where the polysaccharide gum is a xanthan and/or a guar gum, cvi-values of between 7-25 are preferred, and where the polysaccharide gum is sodiumcarboxymethylcellulose, cvi-values of between 3-6 are preferred.

Higher cvi-values are also preferred at higher abrasive silica levels, e.g. at levels of 30-50%, and lower cvi-values at lower abrasive silica levels, e.g. 2-20% by weight of abrasive silica.

The liquid dentifrice of the invention may furthermore contain other optional ingredients, such as anionic, nonionic, zwitterionic and amphoteric surfactants such as soaps, alkylsulphates, alkylbenzene sulphonates, sorbitan esters of fatty acids, sulphobetaines and the like. Flavours, sweeteners, and preservatives may also be included. As preservative formaldehyde is a preferred option, but antimicrobial essential oils containing eugenol, thymol or linalool may also be used as preservative. Other preservatives are benzoic acid esters such as methyl- and propyl parabens (R).

The liquid dentifrice furthermore preferably contains a fluoride source as anticaries agent, such as sodium fluoride or sodium monofluorophosphate in an amount of 0.1-1.5%, preferably 0.8-1.2% by weight.

Furthermore, the liquid dentifrice may contain other anticaries agents such as casein and casein digests, hydroxyapatites, trimetaphosphates; anti-plaque agents such as zinc citrate, triclosan, copper salts and stannouspyrophosphate; anti-calculus agents such as alkalimetal pyrophosphates; vitamins such as vitamin C, and polymers such as polyvinylmethylether—maleic anhydride copolymers, polyacrylates etc.

The invention will further be illustrated by the following examples.

EXAMPLE

The following liquid dentifrices were prepared

|  | A | B | C | D | E | F | G | H | I |
|---|---|---|---|---|---|---|---|---|---|
| Gasil 200 TP | 5 | 10 | — | — | 10 | — | 4 | 10 | — |
| Zeodent 113 | — | — | 20 | 20 | — | 10 | — | — | 10 |
| Xanthan gum | 0.6 | 0.5 | 0.8 | 0.9 | 1.5 | 0.8 | 0.4 | 0.2 | 0.2 |
| Sident 22 S | 10 | 10 | — | — | — | — | 13 | 8 | 14 |
| Sodium laurylsulphate | 1.25 | 1.25 | 1.25 | 1.25 | 1.25 | 1.25 | 1.25 | 1.25 | 1.25 |
| sodium fluoride | 0.2 | 0.2 | 0.2 | 0.2 | 0.2 | 0.2 | 0.2 | 0.2 | 0.2 |
| titaniumdioxide | 1.0 | 1.0 | 1.0 | 1.0 | 1.0 | 1.0 | 1.0 | 1.0 |  |
| formalin (40% formalhyde) | 0.1 | 0.1 | 0.1 | 0.1 | 0.1 | 0.1 | 0.1 | 0.1 | 0.1 |
| flavour | 0.8 | 0.8 | 0.8 | 0.8 | 0.8 | 0.8 | 0.8 | 0.8 | 0.8 |
| saccharine | 0.15 | 0.15 | 0.15 | 0.15 | 0.15 | 0.15 | 0.15 | 0.15 | 0.15 |
| Water | 80.9 | 76.0 | 75.7 | 75.6 | 85.0 | 85.7 | 79.1 | 78.2 | 72.3 |
| P (%) | 0.74 | 0.66 | 1.06 | 1.19 | 1.76 | 0.93 | 0.51 | 0.26 | 0.28 |
| S (%) | 12.36 | 13.16 | 0 | 0 | 0 | 0 | 16.43 | 10.22 | 19.36 |
| cvi | 10.32 | 10.36 | 18.87 | 16.81 | 11.36 | 21.51 | 7.00 | 37.62 | 2.29 |
| Viscosity (Pa.S): |  |  |  |  |  |  |  |  |  |
| A 200-300 |  |  |  |  |  |  |  |  |  |
| B 150-250 |  |  |  |  |  |  |  |  |  |
| C 50-150 |  |  |  |  |  |  |  |  |  |
| D 75-150 |  |  |  |  |  |  |  |  |  |
| E 100-200 |  |  |  |  |  |  |  |  |  |
| F 50-150 |  |  |  |  |  |  |  |  |  |
| G 250-350 |  |  |  |  |  |  |  |  |  |
| H 25-50 |  |  |  |  |  |  |  |  |  |
| I 500-600 |  |  |  |  |  |  |  |  |  |

Products A-G had a viscosity of between 50-400 Pa.s. at 0.1 sec.$^{-1}$, at 25° C., and were stable during storage at 37° C. for a period of 3 months. The viscosity measurements were carried out at 25° .C and at 0.1 sec.$^{-1}$ in a Haake viscometer.

Product H was unstable, and product I was both unstable and too thick. The viscosities of products H and I were 25-50 Pa.s and 500-600 Pa.s. respectively.

I claim:

1. A stable liquid dentifrice composition having a viscosity between at least 50 and up to not more than 500 pa.s so as to hold onto toothbrush bristles once dispensed from a container, the composition comprising from 2 to 50% by weight of a particulate siliceous abrasive cleaning agent having a specific surface area of between 50 and 900 m$^2$/g, stably suspended in an aqueous liquid medium which is substantially free from alcohol and polyol-type humectants with the aid of from 0.25 to 2% by weight of a polysaccharide gum as suspending agent.

2. A composition according to claim 1, further comprising a thickening silica.

3. A composition according to claim 1, having a compositional viscosity index of between 3-30, said compositional viscosity index being $$\frac{20-S}{P},$$

whereby
S = concentration in % of thickening silica, if present, in the aqueous medium, and
P = concentration in % of polysaccharide gum in the aqueous medium.

4. A composition according to claim 3, comprising a xanthan gum as suspending agent, said composition having a compositional viscosity index of between 7 and 25.

5. A composition according to claim 3, comprising sodium carboxymethylcellulose as suspending agent, said composition having a compositional viscosity index of between 3-6.

6. A composition according to claim 1, comprising from 2-50% by weight of a particulate siliceous abrasive material having a specific surface area of between 50 and 900 m$^2$/g and a pore volume of between 0.2 and 0.6 l/kg, from 0-15% by weight of a thickening silica having a specific surface area of between 100 and 400 m$^2$/g and a pore volume of between 1.0 and 2.2 l/kg, stably suspended in an aqueous liquid medium which is substantially free from polyol-type humectants, with the aid of from 0.25% to 2% by weight of a polysaccharide gum as suspending agent.

* * * * *